(12) United States Patent
Fairneny et al.

(10) Patent No.: US 8,849,081 B2
(45) Date of Patent: Sep. 30, 2014

(54) SIDE FIRE LASER ASSEMBLY

(71) Applicant: Boston Scientific Scimed, Inc., Maple Grove, MN (US)

(72) Inventors: Ty Fairneny, Hopkinton, MA (US); Isaac Ostrovsky, Wellesley, MA (US); Michael O'Brien, Cambridge, MA (US); William Asselin, Lunenburg, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 14/246,467

(22) Filed: Apr. 7, 2014

(65) Prior Publication Data

US 2014/0226933 A1     Aug. 14, 2014

Related U.S. Application Data

(63) Continuation of application No. 13/094,554, filed on Apr. 26, 2011, now Pat. No. 8,731,351.

(60) Provisional application No. 61/330,734, filed on May 3, 2010.

(51) Int. Cl.
    *G02B 6/36*     (2006.01)
    *A61B 18/22*    (2006.01)
    *A61B 1/07*     (2006.01)
    *G02B 6/26*     (2006.01)

(52) U.S. Cl.
    CPC .................... *G02B 6/262* (2013.01)
    USPC ................ 385/38; 385/78; 600/182; 606/16; 607/93

(58) Field of Classification Search
    None
    See application file for complete search history.

(56) References Cited

U.S. PATENT DOCUMENTS

| 5,562,657 A | 10/1996 | Griffin |
| 6,520,927 B1 | 2/2003 | Unsworth |
| 2003/0199860 A1 | 10/2003 | Loeb et al. |
| 2007/0106286 A1 | 5/2007 | Harschack et al. |
| 2009/0287199 A1 | 11/2009 | Hanley et al. |
| 2009/0287200 A1 | 11/2009 | Hanley et al. |
| 2009/0326525 A1 | 12/2009 | Hixon et al. |
| 2010/0016845 A1 | 1/2010 | Hanley et al. |

OTHER PUBLICATIONS

International Search Report and Written Opinion issued in PCT International Application No. PCT/US2011/034427 mailed Aug. 25, 2011 (11 pages).

*Primary Examiner* — Jerry Rahll
(74) *Attorney, Agent, or Firm* — Bookoff McAndrews, PLLC

(57) ABSTRACT

Embodiments include an apparatus including an optical fiber having a proximal end and a distal end. The distal end of the optical fiber has a surface configured to emit energy transverse to a longitudinal axis of the optical fiber. The apparatus also includes a tube including a channel, and the distal end of the optical fiber is disposed in the channel of the tube. The apparatus further includes an element disposed at a distal end of the tube such that a pocket is formed in the channel of the tube between the element and the distal end of the optical fiber.

20 Claims, 4 Drawing Sheets

SIDE FIRE LASER ASSEMBLY

This application is a Continuation Application of U.S. patent application Ser. No. 13/094,554, filed Apr. 26, 2011, currently pending, which is a non-provisional Patent Application of and claims the benefit of priority from U.S. Provisional Application No. 61/330,734, filed May 3, 2010, all of which are herein incorporated by reference in their entireties.

FIELD

Embodiments include medical devices and more particularly medical devices including a side fire laser assembly and related methods of use.

BACKGROUND

Side fire laser assemblies may be used for laser-based surgical procedures, for example, to deliver laser energy of a specific wavelength at a specific pulse rate to remove tissue through vaporization. Such procedures may be performed in an aqueous environment, for example, under water.

FIGS. 1 and 2 show a conventional side fire laser assembly 100 including a side fire optical fiber 130. An end 132 of the optical fiber 130 may be polished at a specific angle such that energy is emitted to a side of the optical fiber, as opposed to the end. To permit the laser to emit energy at the correct angle, an air interface is provided at the polished end 132 of the optical fiber 130. As shown in FIG. 1, an air gap 160 is formed in the conventional laser assembly 100 when a capillary tube 150 is fused to the optical fiber 130 and an end 152 of the capillary tube 150 is heated until the end of the capillary tube 150 collapses, thereby forming the air gap 160. As shown in FIG. 2, a metal cap 200 may be placed over the end 152 of the capillary tube 150. During a procedure, as noted below, up to 100 W (watts) of energy may pass through the optical fiber 130 at pulse rates up to 50 Hz (Hertz). This pulsed energy may create vapor bubbles upon exiting the optical fiber 130. These vapor bubbles may collapse back violently onto the face of the optical fiber 130. The metal cap 200 helps to reinforce the capillary tube 150 during energy delivery through the laser assembly 100.

When using this conventional laser assembly 100, a portion of the laser energy may leak from the distal end 132 of the optical fiber 130, thereby reducing the efficiency with which laser energy is delivered to the treatment area in the patient and/or overheating the metal cap 200 that is used to protect the optical fiber 130. For example, this conventional laser assembly can operate at 100 W of average power. This means that, for every second, 100 J (joules) of energy pass through the optical fiber. The laser assembly can operate in a pulse mode with a pulse rate of 50 Hz and a pulse duration of only 200 µs (microseconds). Each pulse therefore delivers 2 J (100 J/50 Hz) and 10,000 W of power (2 J/200 µs=2 J/0.2×10$^{-3}$ s=10× 10$^3$ W). The efficiency of energy transition between the optical fiber and the outside media in the conventional laser assembly may be 96-98%. This means that 2-4% of energy is lost by being converted to heat, creating about 200-400 W of heat for every pulse. Most of the loss by heat generation happens in a very small volume on the end of the capillary tube where the energy beam changes direction and transits from glass into water. If the heat is not dissipated efficiently, the temperature in the end of the optical fiber can rise higher than the structure can handle.

Accordingly, cooling of the device may be needed to operate the laser assembly at a safe temperature. In some instances, the overheating that can occur from laser energy leakage can affect the mechanical and/or optical properties of the end of the optical fiber, the capillary tube, and/or the metal cap. In other instances, the overheating that can occur from laser energy leakage can be sufficiently severe to damage the end of the optical fiber, the capillary tube, and/or the metal cap.

Besides high temperatures, intense vibrations may be generated during each laser pulse. These vibrations may cause glue that attaches the metal caps to the capillary tube to break away. As the glue dislodges, the capillary tube is allowed to vibrate more freely. The vibration of the capillary tube may be so intense that the glass of the capillary tube may begin to break or fracture.

Accordingly, a need exists for a laser assembly that can withstand high temperatures and/or vibrations.

It is to be understood that both the foregoing general description and the following detailed description are exemplary and explanatory only and are not restrictive of the invention.

SUMMARY

In accordance with an embodiment, an apparatus includes an optical fiber having a proximal end and a distal end. The distal end of the optical fiber has a surface configured to emit energy transverse to a longitudinal axis of the optical fiber. The apparatus also includes a tube including a channel, and the distal end of the optical fiber is disposed in the channel of the tube. The apparatus further includes an element disposed at a distal end of the tube such that a pocket is formed in the channel of the tube between the element and the distal end of the optical fiber.

In accordance with another embodiment, a method of forming an apparatus includes disposing a distal end of an optical fiber within a channel in a tube. The optical fiber has a surface configured to emit energy transverse to a longitudinal axis of the optical fiber. The method also includes forming a pocket in the channel of the tube between an element and the distal end of the optical fiber by disposing the element at a distal end of the tube. A distal end of the element protrudes distally from the distal end of the tube.

In accordance with a further embodiment, an apparatus includes an optical fiber having a proximal end and a distal end. The distal end of the optical fiber has a surface configured to emit energy transverse to a longitudinal axis of the optical fiber. The apparatus also includes a tube including a channel, and the distal end of the optical fiber is disposed in the channel of the tube. The tube is disposed in a structure configured to maintain a compressive axial force on the tube.

Additional objects and advantages of the invention will be set forth in part in the description which follows, and in part will be obvious from the description, or may be learned by practice of the invention. The objects and advantages of the invention will be realized and attained by means of the elements and combinations particularly pointed out below.

It is to be understood that both the foregoing general description and the following detailed description are exemplary and explanatory only and are not restrictive of the invention.

BRIEF DESCRIPTION OF THE DRAWINGS

The accompanying drawings, which are incorporated in and constitute a part of this specification, illustrate several embodiments of the invention and together with the description, serve to explain the principles of the invention.

DESCRIPTION OF THE EMBODIMENTS

Reference will now be made in detail to exemplary embodiments of the invention, examples of which are illustrated in the accompanying drawings. Wherever possible, the same reference numbers will be used throughout the drawings to refer to the same or like parts.

The terms "proximal" and "distal" are used herein to refer to the relative positions of the components of an exemplary laser assembly 10. When used herein, "proximal" refers to a position relatively closer to the exterior of the body or closer to the surgeon, or other user, using the laser assembly 10. In contrast, "distal" refers to a position relatively further away from the surgeon, or other user, using the laser assembly 10 or closer to the interior of the body.

The devices and methods described herein are generally related to the use of side-firing optical fibers within the body of a patient. For example, the devices and methods may be suitable for use in treating symptoms related to an enlarged prostate gland, such as a condition known as Benign Prostatic Hyperplasia (BPH). BPH is a common condition in which the prostate becomes enlarged with aging. Laser-based surgical procedures employing side-firing optical fibers and high-power lasers may be used to remove obstructing prostate tissue, e.g., associated with BPH. In these procedures, a doctor may pass the optical fiber through the urethra using a cystoscope, a specialized endoscope with a small camera on the end, and then may deliver multiple pulses of laser energy to destroy some of the enlarged prostate tissue and to shrink the size of the prostate. The devices and methods described herein may be used to treat conditions of the body other than BPH.

Figure 1:
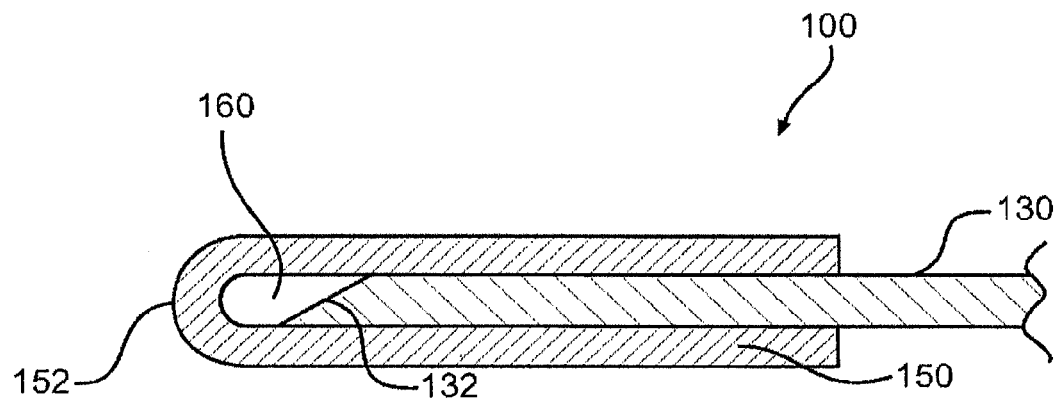
FIG. 1 is a cross-sectional view of a distal end portion of a conventional laser assembly including a capillary tube and optical fiber.
Figure 2:
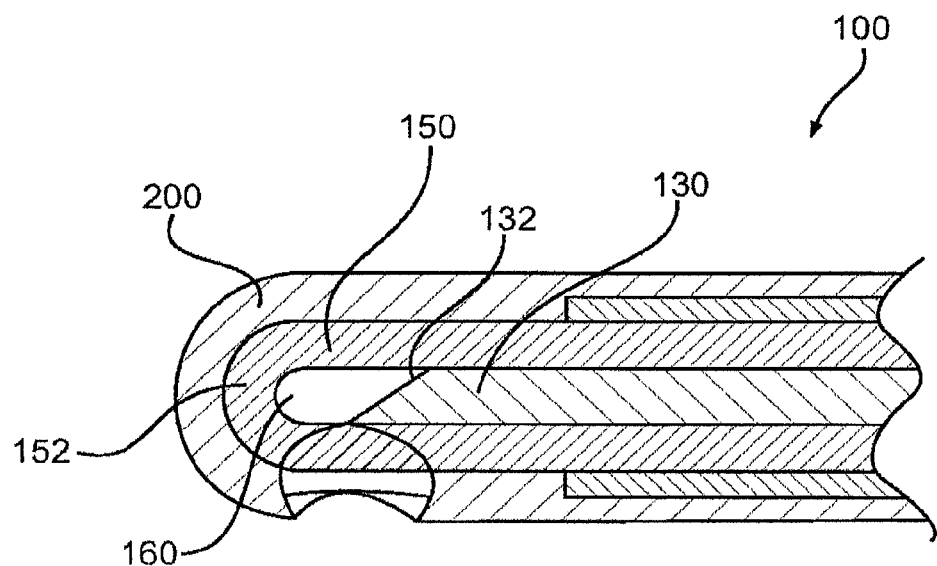
FIG. 2 is a cross-sectional view of the distal end portion of the conventional laser assembly of FIG. 1 with a metal cap disposed over the capillary tube and optical fiber.
Figure 3:
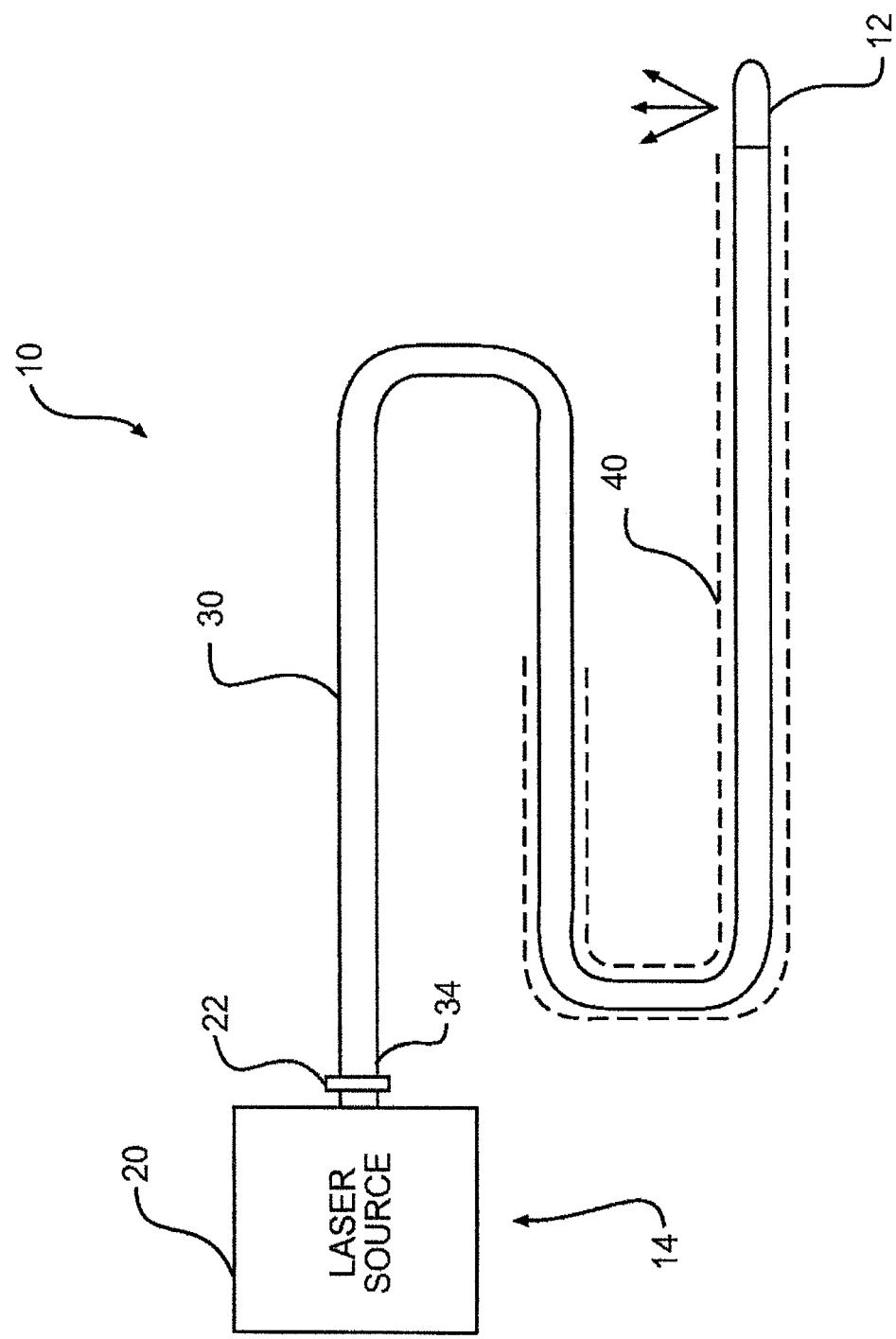
FIG. 3 is a schematic view of a laser assembly, according to an exemplary embodiment of the invention.

FIG. 3 is a schematic drawing of a side fire laser assembly 10 according to an exemplary embodiment. The laser assembly 10 may include a distal end portion 12 and a proximal end portion 14. The laser assembly 10 may also include a laser source 20 and an optical fiber 30. The laser source 20 may be located in the proximal end portion 14 of the laser assembly 10, and the optical fiber 30 may extend between and into the proximal and distal end portions 12, 14 of the laser assembly 10. The laser assembly 10 may be used to transmit laser energy from the laser source 20 to a target treatment area within a patient's body, e.g., near the distal end portion 12 of the laser assembly 10.

The laser source 20 may include at least one laser that may be used to generate laser energy for surgical procedures. The laser source 20 may include at least one of, for example, a Ho:YAG laser, a neodymium-doped:YAG (Nd:YAG) laser, a semiconductor laser diode, or a potassium-titanyl phosphate crystal (KTP) laser. The laser source 20 may include more than one laser, and more than one laser may be used during a surgical procedure. The laser source 20 may also include a processor that provides timing, wavelength, and/or power control of the laser(s). For example, the laser source 20 may include one or more mechanisms for laser selection, filtering, temperature compensation, and/or Q-switching operations.

The optical fiber 30 may include a distal end 32 (FIGS. 4-7) and a proximal end 34. The proximal end 34 of the optical fiber 30 may be coupled to the laser source 20 in the proximal end portion 14 of the laser assembly 10. For example, the proximal end 34 of the optical fiber 30 may be coupled to the laser source 20 through an optical coupler 22 in or near the proximal end portion 14 of the laser assembly 10. The optical coupler 22 may be, for example, an SMA (SubMiniature version A) connector. The proximal end 34 of the optical fiber 30 may be configured to receive laser energy from the laser source 20 via the optical coupler 22, and the optical fiber 30 may be configured to output the laser energy through the distal end 32 of the optical fiber 30. The optical fiber 30 may include, for example, a core, one or more cladding layers about the core, a buffer layer about the cladding, a jacket, etc. The core may be made of a suitable material for the transmission of laser energy from the laser source 20. The core may be multi-mode and may have a step or graded index profile. The cladding may be a single or a double cladding that may be made of a hard polymer or silica. The buffer may be made of a hard polymer such as Tefzel®, for example. When the optical fiber 30 includes a jacket, the jacket may be made of Tefzel®, for example, or other polymers. The optical fiber 30 may be made of a suitable biocompatible material and may be flexible, for example, to traverse tortuous anatomy in the body.

The laser assembly 10 may also include a suitable catheter or endoscope 40 for inserting the distal end portion 12 of the laser assembly 10 into a patient's body. The endoscope 40 may define one or more lumens. In some embodiments, the endoscope 40 may include a single lumen that may receive various components such as the optical fiber 30. The endoscope 40 may have a proximal end configured to receive the distal end 32 of the optical fiber 30 and a distal end configured to be inserted into a patient's body for positioning the distal end 32 of the optical fiber 30 in an appropriate location for a laser-based surgical procedure. For example, to perform a surgical procedure near the prostate, the endoscope 40 may be used to place the distal end 32 of the optical fiber 30 at or near the prostate gland. The endoscope 40 may be made of a suitable biocompatible material and may include an elongate portion that may be flexible to allow the elongate portion to be maneuvered within the body. The endoscope 40 may also be configured to receive various other medical devices or tools through one or more lumens of the endoscope 40, such as, for example, irrigation and/or suction devices, forceps, drills, snares, needles, etc. In some embodiments, the endoscope 40 may include a fluid channel (not shown) coupled at a proximal end to a fluid source (not shown). The fluid channel may be used to irrigate an interior of the patient's body during a laser-based surgical procedure. In some embodiments, the endoscope 40 may include an optical device (not shown), e.g., including an eyepiece coupled to a proximal end of the endoscope 40. The optical device may include an optical fiber or other image transmission device, e.g., a wireless device, that may be disposed in or on the endoscope 40, e.g., in a lumen or on a distal end of the endoscope 40, to transmit an image signal to the surgeon. Such an embodiment allows a medical practitioner to view the interior of a patient's body through the eyepiece.

FIGS. 4-7 show a method of forming the distal end portion 12 of the laser assembly 10, according to an exemplary embodiment. The distal end portion 12 of the laser assembly 10 may be formed using one or more steps illustrated in FIGS. 4-7, to arrive at a final distal end portion 12 shown in FIG. 7.

Figure 4:
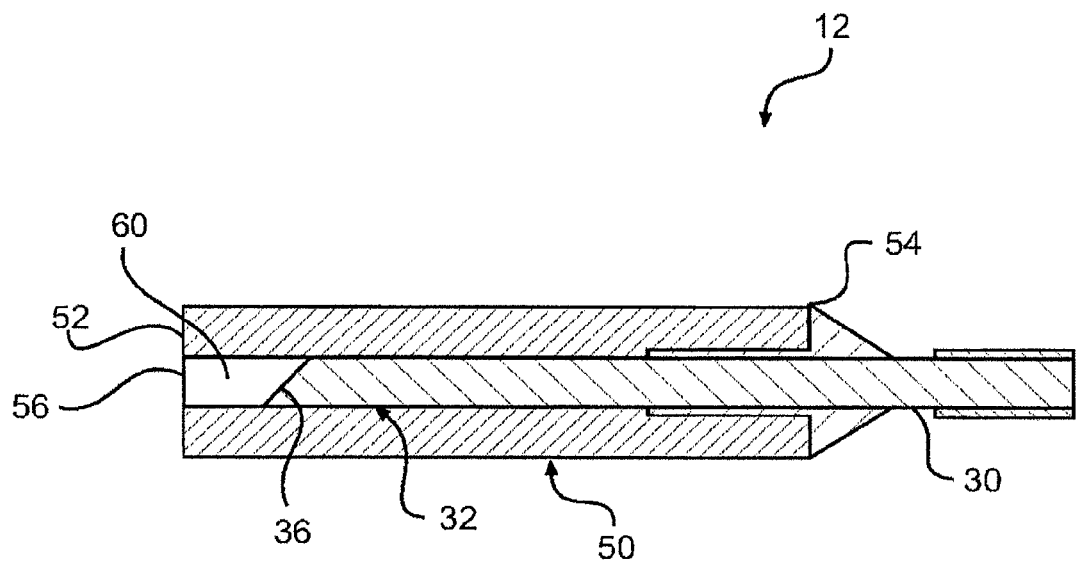
FIG. 4 is a cross-sectional view of a distal end portion of a laser assembly including a capillary tube and optical fiber, according to an exemplary embodiment of the invention.

As shown in FIG. 4, the distal end 32 of the optical fiber 30 may form an angled portion 36 in the distal end portion 12 of the laser assembly 10. The distal end portion 12 of the laser assembly 10 (including the angled portion 36) may be inserted into the patient's body to provide laser treatment. An optical beam (e.g., laser beam including laser energy) may be transmitted from the laser source 20, through the optical fiber 30 from its proximal end 34 to its distal end 32, and then through the angled portion 36 at the distal end 32 of the optical fiber 30. The angled portion 36 may be cleaved and/or polished to an appropriate angle configured to redirect laser energy in a lateral direction for side-firing transmission of laser energy to the area of treatment in the patient's body. Thus, the distal end 32 of the optical fiber 30 may include one or more members, elements, or components that may individually or collectively operate to transmit laser energy in a lateral direction offset from a longitudinal axis or centerline of the distal end 32 of the optical fiber 30.

Figure 5:
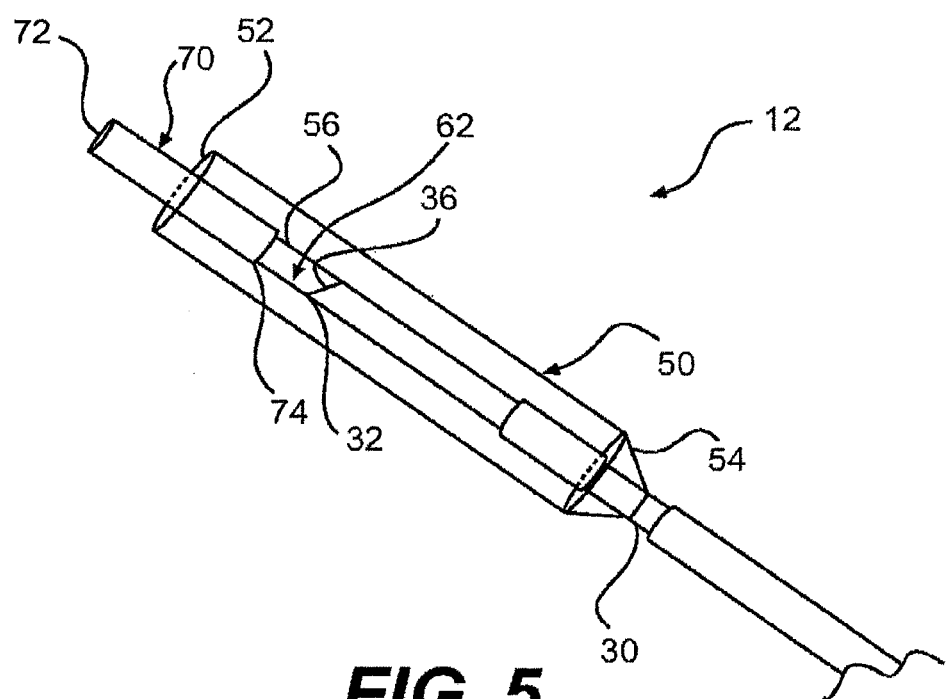
FIG. 5 is a perspective view of the distal end portion of the laser assembly of FIG. 4 with a mandrel.

The distal end 32 of the optical fiber 30 may be disposed within a channel 56 in a capillary tube 50 in the distal end portion 12 of the laser assembly 10. The capillary tube 50 may include a distal end 52 and a proximal end 54, and the channel 56 may extend longitudinally between the distal and proximal ends 52, 54. The capillary tube 50 may be made of, for example, at least one of silica, sapphire, glass, and/or other like materials. An outer surface of the distal end 32 of the optical fiber 30 may be fused or attached to an inner surface of the capillary tube 50. The proximal end 54 of the capillary tube 50 may be formed at an angle to have a frustoconical shape, as shown in FIGS. 4 and 5, or flat. The distal end 52 of the capillary tube 50 may also be formed at an angle to have a frustoconical shape or flat, as shown in FIGS. 4 and 5.

The optical fiber 30 may be disposed through a proximal part of the channel 56 in the capillary tube 50. For example, the distal end 32 of the optical fiber 30 may be inserted into the proximal end 54 of the capillary tube 50 such that the channel 56 remains at least partially empty and the capillary tube 50 is open-ended at its distal end 52, as shown in FIG. 4. As shown, the distal end 52 of the capillary tube 50 is distal to the angled portion 36 of the optical fiber 30. Since the channel 56 is at least partially empty, a gap 60 is formed in the channel 56 at a location that is distal from the distal end 32 of the optical fiber 30. Also, the distal end 52 of the capillary tube 50 may be kept flat, i.e., not rounded, and unmelted, as shown in FIG. 4.

As shown in FIG. 5, a mandrel 70 or other like-shaped cylinder or rod may be inserted into the open end of the channel 56 in the capillary tube 50 in the distal end portion 12 of the laser assembly 10. The mandrel 70 may include a distal end 72 and a proximal end 74. An outer surface of the proximal end 74 of the mandrel 70 may be attached, such as with an adhesive or glue, to an inner surface of the capillary tube 50. At least a portion of the mandrel 70 and/or a coating on the mandrel 70 may include a material that aids in the absorption or conduction of energy or heat away from the interior of the capillary tube 50. The mandrel 70 may dissipate the energy or heat. For example, at least a portion of the mandrel 70 and/or a coating on the mandrel 70 may be made of, for example, a metal, metal alloy, and/or other thermally conductive material. Some nonlimiting examples include silver, copper, nickel, aluminum, stainless steel, titanium, tungsten (which has a higher melting point temperature), beryllium copper, etc.

The mandrel 70 may be disposed in a distal part of the channel 56 in the capillary tube 50. Furthermore, the proximal end 74 of the mandrel 70 may be inserted through the distal end 52 of the capillary tube 50 such that the channel 56 in the capillary tube 50 is at least partially empty between the proximal end 74 of the mandrel 70 and the distal end 32 of the optical fiber 30, as shown in FIG. 5. Thus, an air pocket 62 may be formed between the proximal end 74 of the mandrel 70 and the distal end 32 of the optical fiber 30. The mandrel 70 and the optical fiber 30 act as seals at the respective ends of the channel 56 of the capillary tube 50 to form the air pocket 62. Accordingly, it is not necessary to melt the distal end 52 of the capillary tube 50 to form the air pocket 62. The mandrel 70 extends past and protrudes from the distal end 52 of the capillary tube 50 so that the distal end 72 of the mandrel 70 is distal to the distal end 52.

The mandrel 70 may conduct heat produced through the energy transition from the optical fiber 30 to the surrounding water environment, as described above, more efficiently. As a result, the temperature of the distal end portion 12 of the laser assembly 10 may be prevented from increasing too high, and the mandrel 70 acts as a heat sink. For example, heat may be conducted from the distal end 32 of the optical fiber 30, through the air pocket 62, through the mandrel 70, and then to the water environment surrounding the distal end portion 12 of the laser assembly 10. Thus, heat may be conducted out of the channel 56 of the capillary tube 50, and the temperature increase in the capillary tube 50 may be reduced (as compared to conventional devices), substantially inhibited, and/or prevented, which prevents overheating of the capillary tube 50 and/or the optical fiber 30.

As a result, providing the mandrel 70 in the distal end portion 12 of the laser assembly 10 allows, for example, an open-ended capillary tube 50 that is not melted at its tip, transfer of heat from inside the capillary tube 50 to the cooler water environment surrounding the distal end portion 12 of the laser assembly 10 through the thermally conductive mandrel 70, and/or absorption of a majority of stray laser energy that may escape through the distal end 32 of the optical fiber 30.

Figure 6:
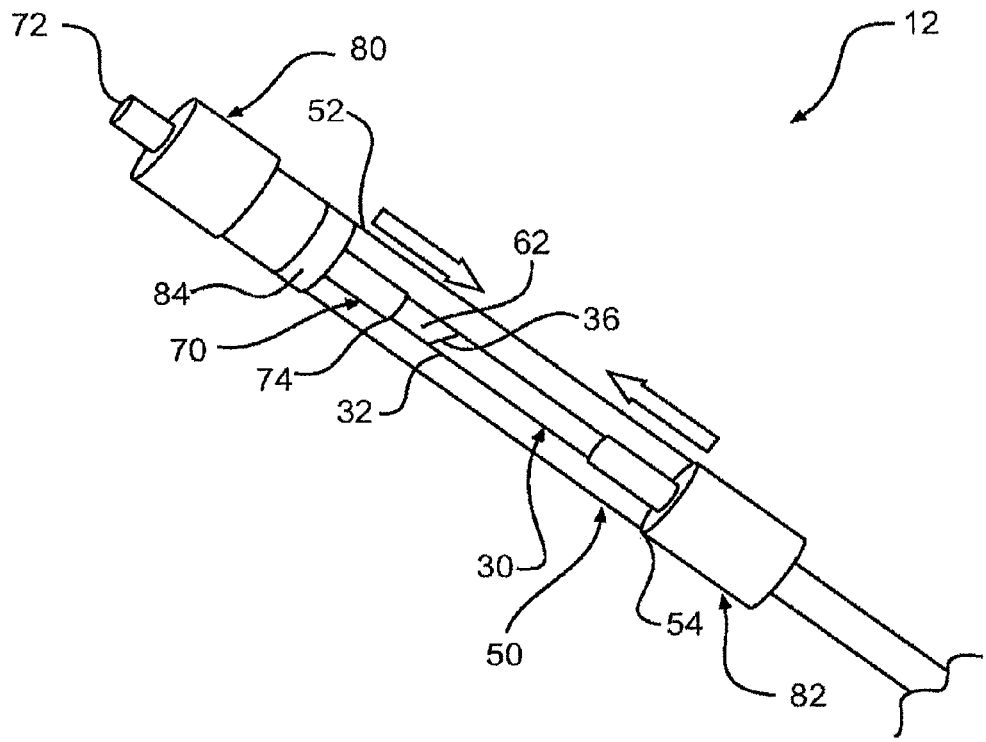
FIG. 6 is a perspective view of the distal end portion of the laser assembly of FIG. 4 with components for reducing vibration of the distal end portion.

As shown in FIG. 6, a first component 80 may be disposed around the mandrel 70 and against the distal end 52 of the capillary tube 50 in the distal end portion 12 of the laser assembly 10. Alternatively, the first component 80 may be disposed against the distal end 72 of the mandrel 70, around the distal end 52 of the capillary tube 50, or in other positions that allow the first component 80 to exert a force against the capillary tube 50 in the proximal direction. As a result, the first component 80 may assist in providing a compressive load on the capillary tube 50 along its longitudinal axis.

A second component 82 may be disposed against the proximal end 54 of the capillary tube 50 and around the optical fiber 30 in the distal end portion 12 of the laser assembly 10. Alternatively, the second component 82 may be disposed around the proximal end 54 of the capillary tube 50, or in other positions that allow the second component 82 to exert a force against the capillary tube 50 in the distal direction. As a result, the second component 82 may also assist in providing a compressive load on the capillary tube 50 along its longitudinal axis.

The first and second components 80, 82 may be made of, for example, a thermally conductive material, such as metal or metal alloy, and/or other like materials as described above. As a result, the first and second components 80, 82 may transfer heat from the capillary tube 50 to the cooler water environment surrounding the distal end portion 12 of the laser assembly 10. Also, the first and second components 80, 82 may sandwich the capillary tube 50, and a compressive axial load may be applied to the capillary tube 50 via the first and second components 80, 82. The compressive axial load may be applied to the capillary tube 50 by forcing together the first and second components 80, 82, for example, using a tool or a machine (e.g., to apply a predetermined load), or by hand as known in the art. It is to be understood that other suitable structures known in the art that are capable of applying or transmitting a compressive axial load on the capillary tube 50 may be used.

A gasket 84 may be disposed between the first component 80 and the distal end 52 of the capillary tube 50, and around the mandrel 70. Alternatively, an additional gasket (not shown) may be disposed between the second component 82 and the proximal end 54 of the capillary tube 50. The gasket 84 may be made, for example, of rubber and/or other compressible materials, and/or other materials that allow the gasket 84 to act to relieve strain on the capillary tube 50, e.g., when high pressure forces from vibrations act on the capillary tube 50. The gasket(s) 84 may include a hole through which the mandrel 70, as shown in FIGS. 6 and 7, or the optical fiber 30 may be inserted.

Figure 7:
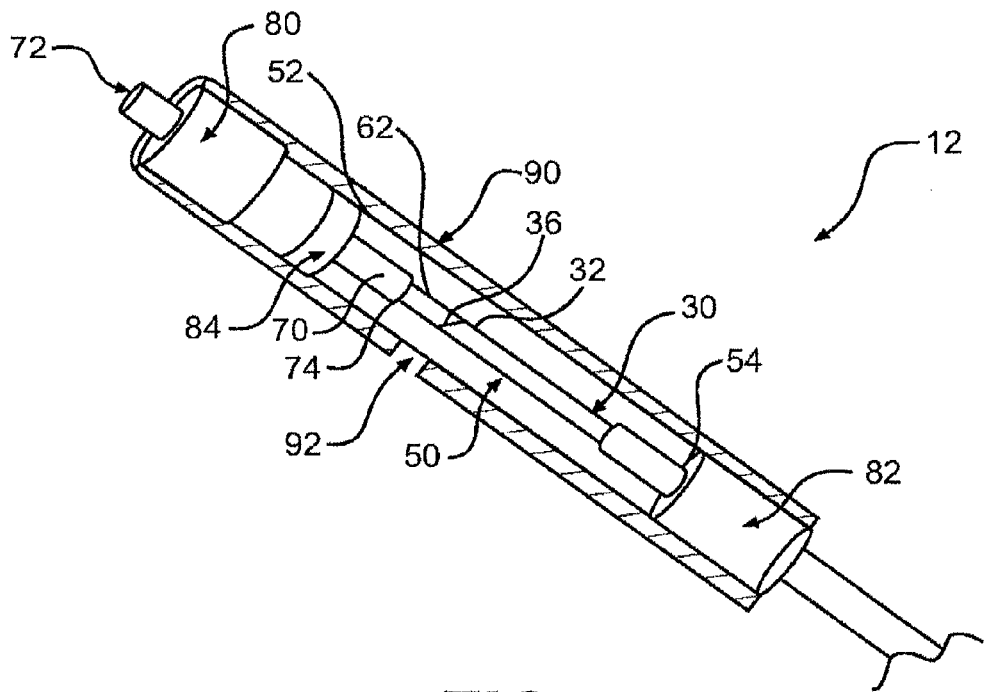
FIG. 7 is a perspective view of the distal end portion of the laser assembly of FIG. 4 with a cap.

The first component 80 may include a channel that receives the mandrel 70, as shown in FIGS. 6 and 7. For example, the first component 80 may be cylindrical. The first component 80 may have a varying cross-section. For example, the outer surface of the first component 80 may have a stepped configuration as shown in FIGS. 6 and 7, which includes two sections with outer surfaces having different diameters, or may be tapered. Alternatively, the first component 80 may have a constant cross-section, as shown in connection with the second component 82 in FIGS. 6 and 7. The channel or proximal end of the first component 80 may be connected to the mandrel 70, the gasket 84, and/or the capillary tube 50 (e.g., the distal end 52, if no gasket 84 is provided) using, for example, an adhesive or glue, by friction fit, etc.

As shown in FIGS. 6 and 7, the first component 80 and the gasket 84 may be inserted over the mandrel 70 so that the distal end 72 of the mandrel 70 extends past and protrudes from a distal end of the first component 80, and so that the distal end 72 of the mandrel 70 is distal to the distal end of the first component 80. Alternatively, the first component 80 and/or the gasket 84 may not include a channel or hole, and the mandrel 70 may abut the first component 80 (or the gasket 84) such that the distal end 72 of the mandrel 70 is proximal to the first component 80 (or the gasket 84). As another alternative, the first component 80 may include a channel that extends only partially through the first component 80, and the mandrel 70 may be inserted into the channel so that the distal end 72 of the mandrel 70 is disposed inside the first component 80 between the distal and proximal ends of the first component 80.

The second component 82 may include a channel that receives the optical fiber 30, as shown in FIGS. 6 and 7. For example, the second component 82 may be cylindrical. The second component 82 may be of constant cross-section, as shown in FIGS. 6 and 7, or of varying cross-section, as described above in connection with the first component 80. The channel or the distal end of the second component 82 may be connected to the optical fiber 30, a gasket (if provided), and/or the capillary tube 50 (e.g., the proximal end 54) using, for example, an adhesive or glue, by friction fit, etc.

As noted above, the distal end 52 and/or proximal end 54 of the capillary tube 50 may be formed at an angle (e.g., having a frustoconical shape) or flat. Accordingly, the gasket(s) 84 and respective ends of the first and second components 80, 82 may also be formed at an angle (e.g., having a surface configured to correspondingly receive the frustoconical shape of the ends 52, 54 of the capillary tube 50) or flat, as shown in FIGS. 6 and 7.

As shown in FIG. 7, after applying the compressive axial load using the first and second components 80, 82, a supportive cap 90 or overtube may be inserted over and attached to the first and second components 80, 82, the respective gasket(s) 84, and/or the capillary tube 50 in the distal end portion 12 of the laser assembly 10. Thus, the cap 90 may serve as a distal casing for and/or may enclose the first component 80, the second component 82, the respective gasket(s) 84, and/or the capillary tube 50. The cap 90 may include a hypotube or other structure sized appropriately to receive and hold the different components together. The cap 90 may connect to the first and second components 80, 82, the respective gasket(s) 84, and/or the capillary tube 50 using, for example, an adhesive or glue, by friction fit, etc. The cap 90 may also include a window 92, for example, laser cut in the cap 90, for the energy delivery from the angled portion 36 of the optical fiber 30 through the cap 90. The cap 90 may be made, for example, of a biocompatible and thermally conductive material, such as metal or metal alloy, and/or other like materials as described above. The cap 90 may have a length extending from a proximal end of the second component 82 to a distal end of the first component 80, as shown in FIG. 7. Alternatively, the cap 90 may extend distally from the proximal end of the second component 82 to abut the step midway between the proximal and distal ends of the first component 80.

The cap 90 may assist in holding the capillary tube 50 sandwiched between the first and second components 80, 82 and may assist in maintaining the compressive axial load on the capillary tube 50 applied by the first and second components 80, 82. The compressive axial load may reduce the amount of vibrations in the distal end portion 12 of the laser assembly 10. As noted above, each laser pulse from the laser source 20 is capable of generating very intense vibrations, and the vibrations on the capillary tube 50 may cause the capillary tube 50 to break or fracture. Since the compressive axial load applied by the first and second components 80, 82 may reduce these vibrations, providing the first and second components 80, 82 may prevent breakage or fracture of the capillary tube 50.

As described above, the distal end portion 12 of the laser assembly 10 may be formed using one or more steps illustrated in FIGS. 4-7. For example, in some embodiments, the distal end portion 12 of the laser assembly 10 may be formed using the steps shown in FIGS. 4 and 5 with respect to inserting the mandrel 70 into the capillary tube 50 without applying a compressive axial force as shown in FIGS. 6 and 7. In other embodiments, the distal end portion 12 of the laser assembly 10 may be formed using the steps shown in FIGS. 6 and 7 with respect to applying a compressive axial force without inserting the mandrel 70 into the capillary tube 50.

Any aspect set forth in any embodiment may be used with any other embodiment set forth herein. Every device and apparatus set forth herein may be used in any suitable medical procedure, may be advanced through any suitable body lumen and body cavity, and may be used for treatment of any suitable body portion. For example, the apparatuses and methods described herein may be used in any natural body lumen or tract, including those accessed orally, vaginally, or rectally.

It will be apparent to those skilled in the art that various modifications and variations can be made in the disclosed systems and processes without departing from the scope of the invention. Other embodiments of the invention will be apparent to those skilled in the art from consideration of the specification and practice of the invention disclosed herein. It is intended that the specification and examples be considered as exemplary only. The following disclosure identifies some other exemplary embodiments.

In some embodiments, an apparatus may include an optical fiber having a proximal end and a distal end. The distal end of the optical fiber may have a surface configured to emit energy transverse to a longitudinal axis of the optical fiber. The apparatus may also include a tube including a channel, and the distal end of the optical fiber may be disposed in the channel of the tube. The apparatus may further include an element disposed at a distal end of the tube such that a pocket is formed in the channel of the tube between the element and the distal end of the optical fiber.

In some embodiments, the element may form a seal on the distal end of the tube.

In some embodiments, a proximal end of the element may be disposed within a distal end of the tube.

In some embodiments, the element may include or be coated with a material configured to transfer heat from inside the tube to outside the tube.

In some embodiments, the element may include or be coated with a material configured to conduct energy transmitted through the distal end of the optical fiber.

In some embodiments, the element may be a metal rod.

In some embodiments, the pocket may be an air pocket.

In some embodiments, the distal end of the tube may be cylindrical and open-ended.

In some embodiments, the apparatus may further include a laser source. The proximal end of the optical fiber may be configured to be coupled to the laser source, and the apparatus may be a laser assembly.

In some embodiments, the tube may be compressed under a compressive axial force.

In some embodiments, the apparatus may further include a first component disposed at a distal end of the tube and a second component disposed at a proximal end of the tube. The first and second components may be configured to apply the compressive axial force on the tube.

In some embodiments, the apparatus may further include a cap configured to attach the first and second components to the tube.

In some embodiments, the apparatus may further include at least one gasket disposed between the tube and at least one of the first and second components.

In some embodiments, a method of forming an apparatus may include disposing a distal end of an optical fiber within a channel in a tube. The optical fiber may have a surface configured to emit energy transverse to a longitudinal axis of the optical fiber. The method may also include forming a pocket in the channel of the tube between an element and the distal end of the optical fiber by disposing the element at a distal end of the tube. A distal end of the element may protrude distally from the distal end of the tube.

In some embodiments, the method may further include forming a seal between the element and the distal end of the tube, and the seal may prevent fluid from entering the channel in the tube.

In some embodiments, the method may further include applying a compressive axial force on the tube and inserting the compressed tube into a tubular structure to maintain the compressive axial force on the tube.

In some embodiments, applying the compressive axial force on the tube may include disposing a first component near the distal end of the tube and disposing a second component near a proximal end of the tube. The compressive axial force may be applied to the tube using the first and second components.

In some embodiments, an apparatus may include an optical fiber having a proximal end and a distal end. The distal end of the optical fiber may have a surface configured to emit energy transverse to a longitudinal axis of the optical fiber. The apparatus may also include a tube including a channel. The distal end of the optical fiber may be disposed in the channel of the tube, and the tube may be disposed in a structure configured to maintain a compressive axial force on the tube.

In some embodiments, the structure configured to maintain the compressive axial force on the tube may include a first component disposed at a distal end of the tube and a second component disposed at a proximal end of the tube. The first and second components may be configured to apply the compressive axial force on the tube.

In some embodiments, the structure configured to maintain the compressive axial force on the tube may further include a cap configured to attach the first and second components to the tube.

What is claimed is:

1. An apparatus comprising:
    an optical fiber having a proximal end and a distal end, the distal end of the optical fiber having a surface configured to emit energy at an off-axis angle relative to a longitudinal axis of the optical fiber;
    a tube including a channel, the distal end of the optical fiber being disposed in the channel of the tube, wherein the tube is maintained under a compressive axial force during use; and
    an element disposed at a distal end of the tube and configured to form a pocket in the channel of the tube between the element and the distal end of the optical fiber.

2. The apparatus of claim 1, wherein the element includes a material configured to transfer heat from inside the tube to outside the tube.

3. The apparatus of claim 1, wherein the element is a metal rod.

4. The apparatus of claim 1, wherein the pocket is an air pocket.

5. The apparatus of claim 1, wherein the distal end of the tube is cylindrical and open-ended.

6. The apparatus of claim 1, wherein a distal end of the element extends distally of a distal end of the tube.

7. The apparatus of claim 1, wherein a proximal end of the tube comprises a frustoconical shape.

8. The apparatus of claim 1, wherein an outer surface of the element is coupled to an inner surface of the tube via at least one of glue or adhesive.

9. The apparatus of claim 1, further including:
    a laser source, the proximal end of the optical fiber being configured to be coupled to the laser source, and the apparatus being a laser assembly.

10. An apparatus comprising:
    a tube having a first end, a second end, and a channel extending between the first and second ends, wherein the tube is compressed under a compressive axial force during use;
    an optical fiber having a proximal end and a distal end, the distal end of the optical fiber having a surface configured to emit energy at an off-axis angle relative to a longitudinal axis of the optical fiber, the optical fiber being located within the first end of the channel; and
    an element being located within the second end of the channel.

11. The apparatus of claim 10, wherein a distal end of the element extends distally of a distal end of the tube.

12. The apparatus of claim 10, wherein the element is coated with a material configured to transfer heat from inside the tube to outside the tube.

13. The apparatus of claim 10, further comprising:
a first component positioned proximate the second end of the tube and a second component positioned proximate the first end of the tube, wherein each of the first and second components are configured to facilitate application of the compressive axial force on the tube.

14. The apparatus of claim 13, further comprising:
at least one compressible gasket positioned between the first component and the second end of the tube, or between the second component and the first end of the tube.

15. The apparatus of claim 10, further comprising:
an overtube enclosing the first and second components and the tube.

16. The apparatus of claim 15, wherein the overtube comprises a hypotube.

17. The apparatus of claim 15, wherein the overtube includes a window extending through a side wall of the overtube and configured to pass energy emitted by the optical fiber therethrough.

18. An apparatus comprising:
a tube having a first end, a second end, and a channel extending between the first and second ends, wherein the tube is secured with a compressive axial preload;
an optical fiber having a proximal end and a distal end, the distal end of the optical fiber having a surface configured to emit energy at an off-axis angle relative to a longitudinal axis of the optical fiber, the optical fiber being located within the first end of the channel;
an element being located within the second end of the channel; and
an overtube enclosing the tube and configured to maintain the compressive axial preload on the tube.

19. The apparatus of claim 18, wherein the element is a metal rod.

20. The apparatus of claim 18, wherein the element is coated with a material configured to conduct energy transmitted through the distal end of the optical fiber.

* * * * *